United States Patent [19]

Friedlander et al.

[11] Patent Number: 4,870,094
[45] Date of Patent: Sep. 26, 1989

[54] SUBSTITUTED IMIDAZOLES AND TRIAZOLES

[75] Inventors: Barry T. Friedlander, Guelph, Canada; Robert A. Davis; Allen R. Blem, both of Cheshire, Conn.

[73] Assignees: Uniroyal Chemical Company, Inc., Middlebury, Conn.; Uniroyal Chemical LTD/LTEE, Don Mills, Canada

[21] Appl. No.: 666,409

[22] Filed: Oct. 30, 1984

Related U.S. Application Data

[63] Continuation-in-part of Ser. No. 606,025, May 2, 1984, abandoned.

[51] Int. Cl.$^4$ .................. A01N 43/653; A01N 43/50; C07D 405/06; C07D 409/06
[52] U.S. Cl. .................................... 514/383; 514/397; 548/262; 548/336
[58] Field of Search ................ 548/262, 336; 514/383, 514/397

[56] References Cited

U.S. PATENT DOCUMENTS

| | | | |
|---|---|---|---|
| 4,366,152 | 12/1982 | Kramer et al. | 548/101 |
| 4,479,004 | 10/1984 | Hubele et al. | 548/262 |
| 4,559,355 | 12/1985 | Kraatz et al. | 514/383 |

FOREIGN PATENT DOCUMENTS

| | | | |
|---|---|---|---|
| 0016587 | 10/1980 | European Pat. Off. | 548/336 |
| 0061789 | 10/1982 | European Pat. Off. | 548/262 |
| 0061794 | 10/1982 | European Pat. Off. | 548/336 |
| 0102578 | 3/1984 | European Pat. Off. | 548/262 |
| 2098607 | 11/1982 | United Kingdom | 548/262 |

*Primary Examiner*—Glennon H. Hollrah
*Assistant Examiner*—Patricia L. Morris
*Attorney, Agent, or Firm*—Raymond D. Thompson

[57] ABSTRACT

A compound of the formula

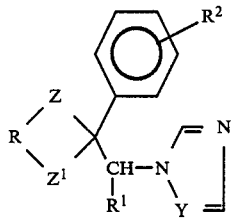

where Z and $Z^1$ are the same or different and are oxygen, sulfur, SO, $SO_2$, or $NR^3$; except that Z and $Z^1$ are not simultaneously oxygen, also, if Z or $Z^1$ is sulfur then the other of Z and $Z^1$ cannot be $NR^3$; Y is nitrogen or CH; R is linear or branched $C_2$-$C_{12}$ alkylene; $R^1$ is hydrogen, $C_1$-$C_4$ alkyl, benzyl or phenyl; $R^2$ is phenyl, phenoxy, phenylthio, phenylsulfinyl, phenylsulfonyl, phenylamino, benzyl, phenoxy substituted with halo, $C_1$-$C_4$ alkyl, $C_1$-$C_4$ alkoxy, nitro, cyano, trihalomethyl or mono-, di- or trihalomethoxy or phenyl substituted with halo, $C_1$-$C_4$ alkyl, $C_1$-$C_4$ alkoxy, nitro, cyano, trihalomethyl or mono-, di- or trihalomethoxy; and $R^3$ is hydrogen or $C_1$-$C_6$ alkyl, is disclosed.

A process for forming this compound is also taught. In the process a substituted azole compound of the formula

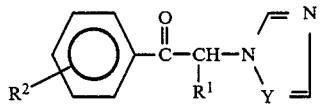

where Y, $R^1$ and $R^2$ have the meanings given above, is reacted with a compound having the formula

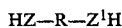

where Z, $Z^1$, R and $R^3$ have the meanings and restrictions given above except Z and $Z^1$ cannot be SO or $SO_2$. Compounds having the meanings SO or $SO_2$ for Z or $Z^1$ are obtained by an additional oxidation step.

A process for controlling fungi employing a fungicidally effective amount of the compound of this invention is recited.

A composition comprising the compound of this invention plus an inert carrier therefore is also set forth.

9 Claims, No Drawings

SUBSTITUTED IMIDAZOLES AND TRIAZOLES

REFERENCE TO RELATED APPLICATION

This is a continuation-in-part application of U.S. patent application, Ser. No. 606,025 filed May 2, 1984, now abandoned.

BACKGROUND OF THE DISCLOSURE

1. Field of the Invention

The instant invention is directed to a new class of substituted imidazoles and triazoles. More particularly, the instant invention is directed to a new class of imidazoles and triazole compounds useful as fungicides.

2. Background of the Prior Art

The economic loss accompanying fungicidal attack on plants is evidenced by the continual development of new compounds employed as fungicides. However, this development continues unabated due to the need to develop broad-based fungicides which are effective against all types of fungi which attack plants and vegetation.

Among the many classes and types of compounds developed for use as fungicides are various classes of substituted imidazoles and triazoles. For example, European Patent Application 29,355 discloses azole compounds, outside the range of the present invention. European Patent Application 92,158 teaches a class of thiazolidine compounds which are recited to have use as a fungicide. European Patent Applications 61,789 and 61,794, which are substantially identical, teach azole substituted fungicides. U.K. Patent Application 2,098,607 sets forth a class of arylphenyl ether derivatives useful in the control of phytopathogenic microorganisms as well as an antimycotic and/or anticonvulsive and anxiolytic pharmaceutical agent. U.S. Pat. No. 3,575,999 recites a class of imidazole derivatives having fungicidal activity. Other substituted triazoles are disclosed in the art as useful as antimicrobial agents. For example, U.S. Pat. Nos. 4,079,062 and 4,402,963 disclose triazole substituted compounds having utility in this application.

A unique problem of many of the compounds known in the art is that in addition to possessing fungicidal characteristics, they also provide plant growth regulation. Oftentimes, such a characteristic is desirable. A fungicidal agent, however, has as its purpose the protection of plant or vegetation by eliminating attack from fungi. A compound effective as a fungicide which is also effective as a plant growth regulant stunts plant growth. In such cases it can be easily appreciated that the cure, if not worse than the disease, is no improvement over the disease.

It is apparent that a new class of fungicidal agents, effective against a wide variety of fungi, is needed in the agricultural chemical art. A class of compounds which not only attack a wide range of fungi, but do not have any adverse effects on plant growth, is particularly desirable.

SUMMARY OF THE INVENTION

The instant invention is directed to a new class of imidazole and triazole substituted compounds whose activity against a wide spectrum of fungi is greater than the imidazole and triazole substituted compounds of the prior art. In addition, the compounds of the present invention are characterized by the absence of plant growth regulant activity. Thus, the plants and vegetation, protected against fungi by the compounds of this invention, do not suffer any adverse effect by the protective presence of these compounds.

In accordance with the instant invention, a compound having the formula

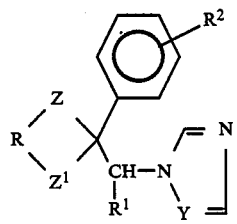

where Z and $Z^1$ are the same or different and are oxygen, sulfur, SO, $SO_2$, or $NR^3$; except Z and $Z^1$ are not simultaneously oxygen and if Z or $Z^1$ is sulfur then the other of Z and $Z^1$ cannot be $NR^3$; Y is N or CH; R is a linear or branched $C_2$-$C_{12}$ alkylene; $R^1$ is hydrogen or $C_1$-$C_4$ alkyl, benzyl or phenyl; $R^2$ is phenyl, phenoxy, phenylthio, phenylsulfinyl, phenylsulfonyl, phenylamino, benzyl, phenoxy substituted with halo, $C_1$-$C_4$ alkyl, $C_1$-$C_4$ alkoxy, nitro, cyano, trihalomethyl or mono-, di- or trihalomethoxy or phenyl substituted with halo, $C_1$-$C_4$ alkyl, $C_1$-$C_4$ alkoxy, nitro, cyano, trihalomethyl or mono-, di- or trihalomethoxy; and $R^3$ is hydrogen or $C_1$-$C_6$ alkyl.

The instant invention is furthermore directed to a process for controlling fungi by the application of a fungicidally effective amount of the compound recited above.

The invention is still further characterized by a composition which comprises the compound recited above with a carrier therefor. This composition is effective as a fungicide.

Yet another aspect of the present invention is a process for forming the compound of this invention. In this process, an azoleketone of the formula

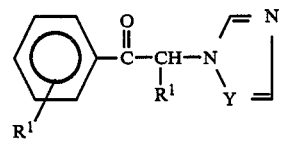

where Y, $R^1$ and $R^2$ have the meanings given above for the definition of the compound formed in the reaction is reacted with a compound having the formula

HZ—R—$Z^1$H where R, Z and $Z^1$ have the meanings given above for the compound of the invention including the limitations included therein except that Z and $Z^1$ cannot be SO or $SO_2$.

DETAILED DESCRIPTION

The present invention is directed to a class of compounds having the formula

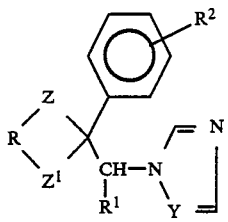

wherein Z and $Z_1$ are the same or different and are oxygen, sulfur, SO, $SO_2$, or $NR^3$; except that Z and $Z^1$ are not simultaneously oxygen, also, if Z or $Z^1$ is sulfur then the other of Z and $Z^1$ cannot $NR^3$; Y is nitrogen or CH; R is linear or branched $C_2$-$C_{12}$ alkylene; $R^1$ is hydrogen, $C_1$-$C_4$ alkyl, benzyl or phenyl; $R^2$ is phenyl, phenoxy, phenylthio, phenylsulfinyl, phenylsulfonyl, phenylamino, benzyl, phenoxy substituted with halo, $C_1$-$C_4$ alkyl, $C_1$-$C_4$ alkoxy, nitro, cyano, trihalomethyl or mono-, di- or trihalomethoxy or phenyl substituted with halo, $C_1$-$C_4$ alkyl, $C_1$-$C_4$ alkoxy, nitro, cyano, trihalomethyl or mono-, di- or trihalomethoxy; and $R^3$ is hydrogen or $C_1$-$C_6$ alkyl.

More preferably, the compound of this invention is Compound I, where Y is nitrogen; Z is oxygen; $Z^1$ is sulfur or $SO_2$; R is $C_2$-$C_5$ linear or branched alkylene; $R^1$ is hydrogen, methyl or phenyl; and $R^2$ is phenyl, phenoxy, phenylthio, phenoxy substituted with fluorine, chlorine, bromine, methyl, methoxy, trifluoromethyl or dichloromethoxy or phenyl substituted with fluorine, chlorine, bromine, methyl, methoxy, trifluoromethyl or dichloromethoxy.

Most preferably, the compound of this invention has the structural formula of Compound I where Y is nitrogen; Z is oxygen; $Z^1$ is sulfur or $SO_2$; R is $C_2$ alkylene; $R^1$ is hydrogen; and $R^2$ is phenyl, phenoxy, phenylthio, phenyl substituted with bromine or phenoxy substituted with bromine.

The compound of this invention, Compound I, is made in accordance with a process in which a compound having the formula

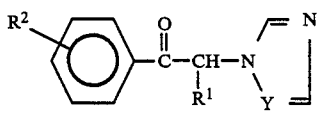

where Y, $R^1$ and $R^2$ have the meanings given above for Compound I is reacted with a compound having the formula

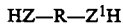    (III)

where R, Z and $Z^1$ have the meanings and restrictions given above for Compound I except that Z and $Z^1$ cannot be SO or $SO_2$.

In this reaction, at least 1 mole, and preferably an excess of Compound III is reacted with 1 mole of Compound II. Usually, the reaction occurs in the presence of an acid catalyst. The acid catalyst employed in this reaction is a Lewis acid. Among the Lewis acids within the contemplation of this invention are methanesulfonic acid, benzenesulfonic acid, p-toluenesulfonic acid, aluminum chloride, zinc chloride, tin chloride, and the like. Of these, p-toluenesulfonic acid is most preferred.

In addition, the reaction is preferably carried out in a solvent mixture, the solvent being an inert organic liquid. Among the preferred inert organic solvents within the contemplation of this invention, are hydrocarbons such as hexane, cyclohexane, heptane, benzene, toluene, xylene, and the like. Other preferred solvents include the lower alkanols, i.e., 1-butanol. Furthermore, chlorinated hydrocarbons such as di-, tri- and tetrachloromethane, dichloroethane, trichloroethane, tetrachloroethane, and the like, may be used. Finally, ethers such as tetrahydrofuran and 1,4-dioxane are additional solvents within the contemplation of this invention. Of these solvents, a solvent mixture of toluene and a lower alkanol, preferably 1-butanol, is particularly preferred.

The reaction, which occurs over a period of one to four days, normally occurs at the reflux temperature of the solvent employed. Azeotropic removal of the water occurs during the reaction period. Final isolation of the product of this reaction, Compound I, is accomplished by conventional means through the precipitated acid salt of Compound I. Alternatively, the product may be isolated from the mother liquor of the reaction mixture.

It is emphasized that the product of this reaction does not encompass all of the compounds of the present invention. Specifically, the meanings of Z and $Z^1$ are limited to oxygen, sulfur and $NR^3$. To obtain the embodiments of the present invention wherein at least one of Z and $Z^1$ is a sulfoxide or sulfone (SO and $SO_2$, respectively) further treatment is required.

In the preferred embodiment wherein the sulfoxide is formed, the product of the reaction, made in accordance with the above procedure, is reacted with an oxidizing agent. Oxidizing agents within the contemplation of this process include the periodates, for example, sodium periodate, potassium periodate, and the like; the peroxides, for example, hydrogen peroxide, sodium peroxide, and the like, and the peroxy acids, for example, peroxybenzoic acid and meta-chloroperoxybenzoic acid. Of these oxidizing agents, m-chloroperoxybenzoic acid is particularly preferred.

In this reaction to produce the sulfoxide embodiment of the compound of this invention, the product produced in the first step, that is, Compound I, where Z and $Z^1$ are not SO or $SO_2$, is reacted with one equivalent of the oxidizing agent, as stated above, preferably, m-chloroperoxybenzoic acid. The time and temperature of the reaction is from one to twenty-four hours and between 0° C. and ambient temperature, respectively. The reaction occurs in the presence of a solvent, i.e., chlorinated hydrocarbons.

In the embodiment wherein a sulfone is produced, that is, where at least one of Z or $Z^1$ is $SO_2$, the same reaction is conducted except that at least two equivalents, and preferably even more, of the oxidizing agent, preferably m-chloroperoxybenzoic acid, is employed. As in the case of sulfoxide production, this step is conducted in the presence of a solvent, which again is preferably a chlorinated hydrocarbon. Of the chlorinated hydrocarbon solvents that may be used in this invention, chloroform or dichloromethane are particularly desirable. The reaction to produce the sulfone, unlike the sulfoxide, occurs at elevated temperature, and preferably at the reflux temperature of the solvent. Again, the reaction occurs over a period of 1 to 24 hours. More preferably, the reaction to produce the sulfone requires 16 to 20 hours.

In a preferred embodiment of the process of this invention, the reactants are Compounds II and III where Y is nitrogen; Z is oxygen; $Z^1$ is sulfur; R is linear or branched $C_2$–$C_5$ alkylene; $R^1$ is hydrogen, methyl or phenyl; and $R^2$ is phenyl, phenylthio, phenyl or phenoxy substituted with fluorine, chlorine, bromine, methyl, methoxy, trifluoromethyl or trichloromethyl.

In a still more preferred embodiment of the process of this invention, the reactants have the structural formula of Compounds II and III where Y is nitrogen; Z is oxygen; $Z^1$ is sulfur; R is $C_2$ alkylene; $R^1$ is hydrogen; and $R^2$ is phenyl, phenylthio, phenoxy, phenyl substituted with bromine or phenoxy substituted with bromine.

The compound of this invention, Compound I, has particular application as a fungicide in the control of fungus growth on plants and vegetation. It is particularly noteworthy that the compounds of this invention are effective against phytopathogenic fungi which are systemic in the plant or deeply embedded in plant tissue. Among these diseases, which are effectively controlled by the compounds of this invention, is powdery mildew disease in barley (*Erysiphe graminis*) and cucumber (*Erysiphe cichoracearum*) and rust diseases such as bean rust (*Uromyces phaseoli*). Certain compounds of this invention have also demonstrated effectiveness against other fungi which case plant disease, including, for example, *Alternaria solani, Cercospora arachidicola, Phytophthora ifestans, Sclerotinia sclerotiorum, Sclerotium rolfsii, Fusarium oxysporum, Helminthosporium maydis* and *Pircularia oryzae*.

In order to effectively employ the compounds of this invention in their prime use, as fungicides, the compounds may be applied neat or in admixture with inert carriers and/or additives to form fungicidally effective compositions. In one embodiment of such a composition, Compound I is combined with a solid inert carrier. Among the inert carriers within the contemplation of this invention, are the mineral silicates, e.g., mica, talc, pyrophylite and the clays. Other solid carriers, within the contemplation of this invention, include vermiculite, charcoal and corn cobs. Solid compositions made by combining the inert carriers recited above with the active compound are applied by well-known methods in the art such as broadcasting, side dressing, soil incorporation and seed treatment.

In another preferred embodiment of the composition of this invention, a liquid composition comprising Compound I and a liquid inert carrier is employed. In this embodiment, the liquid carrier may be a solvent or a suspending agent for the active compound, Compound I. It is emphasized that the carrier itself is inert in terms of providing fungicidal activity.

Among the liquid carriers within the contemplation of this invention are water, alkanols and aromatic solvents such as substituted and unsubstituted phenol, benzene, kerosene, toluene and xylene.

Another preferred embodiment of the liquid composition of this invention is an emulsion formed by dissolving Compound I in a suitable organic solvent and then adding the solvent to water. Of course, a suitable emulsifying agent, a surface active agent which may be anionic, non-ionic or cationic, is added in the formation of the emulsion.

In yet another embodiment of the liquid composition of this invention, Compound I is combined with water to form a dispersion in the absence of an organic solvent. Again, surface-active dispersing agents are employed in the preparation of the suspension.

The surface-active agents effective in the preparation of compositions which include a liquid phase are known to the art. For example, U.S. Pat. No. 2,547,734 provides detailed examples of such agents employed in the emulsions and dispersions of this invention.

In yet another liquid composition of this invention, solutions are prepared for aerosol application of the compound of this invention. These compositions are prepared by dissolving Compound I directly in an aerosol solvent which is a liquid at elevated pressures. The aerosol method involves releasing the aerosol solution in the atmosphere at a pressure at which the carrier is a gas. Alternatively, the aerosol solution may be prepared by first dissolving Compound I in a less volatile solvent and then admixing the thus formed solution with a highly volatile liquid aerosol carrier and proceeding as discussed above.

In another embodiment of the composition of this invention, a two-phase composition is provided. In this application, Compound I is first absorbed on the surface of an inert solid carrier. As stated above, the various mineral silicates are particularly preferred in this application. These inert silicates are then dispersed, in the presence of a dispersing agent, in a suitable non-solvent medium, usually water.

The following examples are given to illustrate the scope of this invention. No express or implied limitation of the invention to these examples is intended, nor should it be assumed.

EXAMPLE 1

1-[(2-[1,1'-Biphenyl]-4-yl-1,3-oxathiolan-2-yl)methyl]-1H-1,2,4-triazole (Compound 1)

To a slurry of 13.1 g of 1-[1,1'biphenyl]-4-yl-2-(1H-1,2,4-triazol-1-yl)ethanone in 175 ml dry toluene and 70 ml 1-butanol was added, with stirring, 7.8 g 2-mercaptoethanol and 12.3 g p-toluenesulfonic acid. The resultant thickened slurry was refluxed under a Dean-Stark [trademark] trap for 72 hours. At this point, no further water was collected. After the reaction was allowed to cool, the solid was filtered out, slurried in dichloromethane and shaken with 10% aqueous sodium hydroxide and once with water. The organic layer was dried and evaporated to leave an oil which solidified on high-vacuum pumping. This solid was triturated with petroleum ether to give 6.7 g of 1-[(2-[1,1'-biphenyl]-4-yl-1,3-oxathiolan-2-yl)methyl]-1H-1,2,4-triazole, the product of this reaction. The melting point of this compound was 85°–90° C.

EXAMPLE 2

1-[(2-[1,1'-Biphenyl]-4-yl-1,3-oxathiolan-2-yl)methyl]-1H-1,2,4-triazole S,S-dioxide (Compound 2)

A solution of 5.1 g 80-85% m-chloroperoxybenzoic acid in 80 ml dichloromethane was added dropwise to a solution of 3.2 g 1-[(2-[1,1'-biphenyl]-4-yl-1,3-oxathiolan-2-yl)methyl]-1H-1,2,4-triazole in 40 ml dichloromethane at room temperature. After the addition was complete, the reaction mixture was refluxed for 24 hours. The volume was then reduced by one-half and the resultant precipitate removed by filtration. The filtrate was washed three times with 5% aqueous sodium bicarbonate, once with water, dried and evaporated to yield 3.1g of 1-[(2-[1,1'-biphenyl]4-yl-1,3-oxathiolan-2-yl)-methyl]-1H-1,2,4-triazole S,S-dioxide product, m.p. 145°–155° C.

EXAMPLE 3

1-[(2-[1,1'-biphenyl]-4-yl-1,3-oxathiolan-2-yl)methyl]-1H-1,2,4-triazole S-oxide (Compound 3)

A solution of 6.1g of 80-85% m-chloroperoxybenzoic acid in 60 ml dichloromethane was added dropwise to a solution of 9.7 g 1-[(2[1,1'-biphenyl]-4-yl-1,3-oxathiolan-2-yl)methyl]-1H-1,2,4-triazole in 45 ml dichloromethane at 0° C. After the addition was complete, the reaction mixture was allowed to warm to ambient temperature and was stirred overnight. The solution was washed three times with 5% aqueous sodium bicarbonate, once with water, dried nd evaporated to leave a white solid. The solid was triturated well with ether to give 8.5 g of 1-[(2-[1,1'-biphenyl]-4-yl-1,3-oxathiolan-2-yl)methyl]-1H-1,2,4-triazole S-oxide m.p. 145°–153° C.

EXAMPLE 4

Preparation of Compounds 4-13

Pursuant to the method described in Examples 1-3, additional compounds within the contemplation of this invention were prepared. These compounds, Compounds 4-13, are tabulated in the Table 1 below. Table 1 also includes Compounds 1-3 made in accordance with the procedure of Examples 1-3, respectively.

TABLE 1

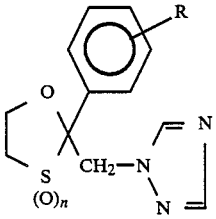

IV

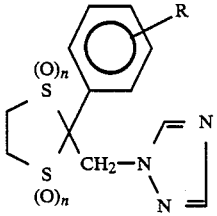

V

| Comp'd No. | Structure | R | n | m.p., °C. |
|---|---|---|---|---|
| 1 | IV | 4-–⟨phenyl⟩ | 0 | 85-90 |
| 2 | IV | 4-–⟨phenyl⟩ | 2 | 145-155 |
| 3 | IV | 4-–⟨phenyl⟩ | 1 | 149-153 |
| 4 | IV | 4-–⟨phenyl⟩-Br | 0 | 135-137 |
| 5 | V | 4-–⟨phenyl⟩ | 0 | 142-143 |
| 6 | V | 4-–⟨phenyl⟩ | 1 | 169-170 |
| 7 | V | 4-–⟨phenyl⟩ | 2 | 190-192 |
| 8 | IV | 4-O-⟨phenyl⟩ | 0 | 120-122 |
| 9 | IV | 4-O-⟨phenyl⟩ | 2 | 127-132 |
| 10 | IV | 4-S-⟨phenyl⟩ | 0 | 118-119 |
| 11 | IV | 4-O-⟨phenyl⟩-Br | 0 | 129-131 |
| 12 | IV | 4-O-⟨phenyl⟩-Br | 2 | 143-145 |
| 13 | V | 4-O-⟨phenyl⟩ | 0 | oil |

Additional compounds are prepared following the procedure of Examples 1-3. These compounds are defined by the structure of Compound I where the radicals have the meanings given in Table 1(A) below.

TABLE 1(A)

| Z | $Z^1$ | R | $R^1$ | $R^2$ | Y |
|---|---|---|---|---|---|
| oxygen | sulfur | $CH_3CHCH_2$ | methyl | phenyl | nitrogen |
| " | $SO_2$ | " | " | " | " |
| " | sulfur | $CH_2CHCH_3$ | " | " | " |
| " | $SO_2$ | " | " | " | " |
| " | sulfur | $CH_3CH_2CH_2CHCH_2$ | phenyl | " | " |
| " | $SO_2$ | " | " | " | " |
| " | sulfur | $CH_2CHCH_2CH_2CH_3$ | " | " | " |

TABLE 1(A)-continued

| Z | Z¹ | R | R¹ | R² | Y |
|---|---|---|---|---|---|
| " | SO₂ | " | " | " | " |
| " | sulfur | CH₂CH₂ | hydrogen | 4-fluorophenyl | " |
| " | SO₂ | " | " | " | " |
| " | sulfur | " | " | 4-chlorophenyl | " |
| " | SO₂ | " | " | " | " |
| " | sulfur | " | " | 4-methylphenyl | " |
| " | SO₂ | " | " | " | " |
| " | sulfur | " | " | 4-methoxyphenyl | " |
| " | SO₂ | " | " | " | " |
| " | sulfur | " | " | 4-trifluoromethylphenyl | " |
| " | SO₂ | " | " | " | " |
| | | | | 4-dichloromethoxyphenyl | " |
| | | | | " | " |

EXAMPLE 5
Control of Powdery Mildew Fungus (Systemic root uptake)

Compounds of the present invention were tested to evaluate their effectiveness in preventing or controlling Powdery Mildew disease of barley (*Erysiphe graminis*) and cucumber P. mildew (*Erysiphe cichoracearum*) by systemic root uptake.

Pots containing several plants of barley (Variety "Herta") and cucumber (Variety "Marketmore 70") were grown to age six days and ten days, respectively. Upon reaching these ages, 45 ml of an emulsion of the compounds of this invention were added to each pot. This 45 ml quantity saturated the soil without significant loss of the emulsion through drainage into the saucers below the pots.

The emulsion was prepared by dissolving the pure compound in 5 to 7 ml of acetone or other suitable solvent, adding one to two drops of an emulsifying agent (i.e., Triton [trademark]X-100) and adding water to yield the appropriate concentrations in parts per million (ppm) of active compound.

In addition, an equal number of pots containing the same barley and cucumber plants were left untreated. These pots were used as controls.

Twenty-four hours after treatment, both barley and cucumber plants were inoculated with the Powdery Mildew fungus, by dusting leaves from infected barley or cucumber plants on each of the treated and untreated plants. Six days thereafter, disease control was evaluated on a 0 to 6 rating scale. A 0 rating was assigned when no disease was evidenced and a 6 rating was given for severe disease. Percent control was computed by comparing the ratings for the treated and untreated plants.

The results of these tests are summarized in Table 2.

TABLE 2
Control of Powdery Mildew By Systemic Root Uptake

| Comp'd No | Dosage, ppm | Percent Control Barley | Cucumber |
|---|---|---|---|
| 1 | 250 | 100 | 100 |
| | 125 | 100 | 66 |
| | 62 | 100 | 0 |
| 2 | 250 | 100 | 100 |
| 5 | 250 | 50 | 0 |
| 6 | 250 | 85 | 40 |
| 7 | 250 | 60 | 0 |
| 8 | 250 | 100 | 100 |
| 9 | 250 | 75 | 90 |
| 10 | 250 | 0 | 0 |
| 11 | 250 | 100 | 65 |
| 12 | 250 | 50 | 40 |

EXAMPLE 6
Control of Barley Powdery Mildew by Foliar Application

Seven to 10 day old plants of "Larker" variety barley, 6–10 plants per pot, were sprayed with the compounds of this invention at dosages indicated. The compounds were applied by first dissolving them in acetone and suspending them in water with the aid of a surfactant or suspending agent. The suspension was then sprayed on duplicate or triplicate pots. A sufficient number of pots, acting as controls were not so treated.

After the pots sprayed were dried, they and the controls were placed in a greenhouse maintained at 21° C. All the pots were inoculated by distributing spores of the mildew fungus over leaves from plants which had previously been infected with mildew disease.

Five days after inoculation, the plants were evaluated by a disease rating of 0 to 6 with 0 and 6 representing no disease and severe disease respectively. Percent control was computed by comparing the treatment scores with the scores for the untreated controls. The results of these tests are summarized in Table 3.

TABLE 3
Control of Barley Mildew by Foliar Treatment

| Compound No. | Dosage, ppm | Percent Control |
|---|---|---|
| 1 | 1000 | 90/100* |
| | 250 | 100 |
| | 125 | 100 |
| | 62 | 100 |
| 2 | 1000 | 100 |
| | 500 | 75/50* |
| | 250 | 100 |
| | 125 | 100 |
| | 62 | 100 |
| 5 | 1000 | 100 |
| 6 | 1000 | 90 |
| 7 | 1000 | 75 |
| 8 | 1000 | 100 |
| 9 | 1000 | 100 |
| 10 | 1000 | 100 |
| 11 | 1000 | 100 |
| 12 | 1000 | 100 |

*Tested twice

EXAMPLE 7

Control of Rice Blast Disease by Foliar Treatment

Three to four week old Bellemont rice plants, 4 to 6 plants per pot, were sprayed with the compounds of this invention at concentrations indicated in the table below. The spray was formulated in accordance with the procedure set forth in Example 6.

Sprayed and unsprayed pots of the plant were inoculated with spores of *Pyricularia oryzae*. Inoculum was prepared to provide 20,000 to 30,000 spores per milliliter. The inoculum was sprayed on the plants with 1 to 2 drops of Tween 20 [trademark] surfactant to insure proper wetting of the plant leaves.

The plants were incubated in a humidity controlled chamber maintained at 21° C. for 24 to 48 hours to allow infection. The plants were transferred to a greenhouse for 5 to 7 days to permit disease development. Disease was manifested by blast lesions on the leaves. Disease control was calculated by either counting lesions, if infection was moderate, or evaluating by the 0-6 rating system defined in earlier examples. The results of this test are tabulated in Table 4.

TABLE 4

Control of Rice Blast Disease

| Compound No. | Dosage, ppm | Percent Control |
|---|---|---|
| 1 | 1000 | 100 |
|   | 250 | 100 |
|   | 125 | 100 |
|   | 25 | 100 |
| 2 | 250 | 100 |
|   | 125 | 100 |
|   | 62 | 100 |
| 8 | 1000 | 100 |
| 9 | 1000 | 100 |
| 10 | 1000 | 65 |
| 11 | 1000 | 100 |
| 12 | 1000 | 100 |

EXAMPLE 8

Control of Bean Rust Fungus

Seven-day-old pinto bean plants (*P. vulgaris*), susceptible to rust disease, were sprayed with a spore suspension (20,000 spores per ml) at the primary leaf stage of growth. The plants were then incubated in a controlled environment chamber at 21° C., with high humidity, for 24 hours, to allow infection. The plants were then removed from the incubator and allowed to dry. Two days after inoculation, most of the infected plants were sprayed with the compounds of this invention, at a dosage of 1,000 ppm. The remaining infected plants were not sprayed, acting as controls. All of the infected plants were then placed in a greenhouse at 70° F. for five days to allow any disease present to be expressed.

Control of disease was assessed by comparing the treated plants with the untreated controls where the plants were rated 0 to 6 as described in earlier examples with the results expressed as percent control of disease. These results are tabulated in Table 5.

TABLE 5

Control of Bean Rust

| Compound No. | Dosage, ppm | Percent Control |
|---|---|---|
| 1 | 1000 | 100 |
|   | 250 | 100 |
|   | 62 | 100 |
| 2 | 1000 | 100 |
|   | 250 | 100 |

TABLE 5-continued

Control of Bean Rust

| Compound No. | Dosage, ppm | Percent Control |
|---|---|---|
|   | 62 | 100 |
| 5 | 1000 | 75 |
| 6 | 1000 | 0 |
| 7 | 1000 | 0 |
| 8 | 1000 | 95 |
| 9 | 1000 | 98 |
| 10 | 1000 | 90 |
| 11 | 1000 | 100 |
| 12 | 1000 | 100 |

EXAMPLE 9

Control of Peanut Cercospora Leafspot by Foliar Treatment

Four week old plants of Virginia peanuts, 3-4 plants per pot, were sprayed with compounds of this invention at dosages of 1000, 500, 250 and 125 ppm. The formulations were applied by directly spraying a suspension of the compound in water onto the plant leaves.

After the plants were sprayed and dried they were inoculated with spores of Peanut Cercospora leafspot (*Cercospora arachidicola*). Inoculum was prepared to give 20,000-30,000 spores per ml. The inoculum was sprayed with 1 to 2 drops of Tween [trademark] 20 surfactant, to aid in wetting leaves. An equal number of pots untreated with the compounds of this invention were inoculated with the leafspot spores. All the inoculated peanut plant pots were incubated in a temperature-humidity controlled chamber at 24° C. for 36 hours. The plants were then placed in a greenhouse for disease development.

After 18-21 days in the greenhouse, symptoms developed which were evaluated on the 0 to 6 disease rating system. Percent control was computed by comparing the scores of the treated pots and untreated control pots. The results of this test are summarized in Table 6.

TABLE 6

Control of Peanut Cercospora Leafspot

| Compound No. | Dosage, ppm | Percent Control |
|---|---|---|
| 1 | 1000 | 99 |
|   | 500 | 99 |
|   | 250 | 99 |
|   | 125 | 93 |
| 2 | 1000 | 99 |
|   | 500 | 99 |
|   | 250 | 99 |
|   | 125 | 98 |

EXAMPLE 10

Control of Barley Blast

About 6 day old barley "Herta" variety plants in pots (about 8 plants per pot) were sprayed with suspensions of compounds of this invention. The plants, and equal numbers of unsprayed controls, were inoculated with spores of *Pyricularia oryzae* in accordance with the procedure of Example 7. The plants were incubated, disease developed and evaluated in accordance with the procedure of Example 7. The results of this test are tabulated in Table 7.

TABLE 7
Control of Barley Blast Disease

| Compound No. | Dosage, ppm | Percent Control |
| --- | --- | --- |
| 1 | 1000 | 100 |
|  | 500 | 100 |
| 2 | 1000 | 100 |
| 5 | 1000 | 100 |
| 6 | 1000 | 40 |
| 7 | 1000 | 75 |

EXAMPLE 11
Control of Eight Fungus Species

Compounds of the present invention were solubilized in acetone at concentrations indicated in Table 8 below. Antibiotic testing discs (11 mm) were dipped in each of these acetone test solutions. The discs were allowed to dry to drive off the acetone solvent. An equal number of discs were untreated to provide a control.

The treated and untreated discs were then placed on agar plates and the test organisms were added to the center of each test disc in the form of a culture plug with the fungus mat in contact with the treated paper of the test disc. The plates were incubated and then evaluated by measuring the diameter of the fungus colony on the treated disc compared to that of the untreated discs. Percent inhibition of growth was calculated. The data generated by this test appear below in Table 8.

TABLE 8

| Compound No. | Dosage, ppm | Cercospora arachidicola | Sclerotinia sclerotium | Fusarium oxysporum | TOMATO EARLY BLIGHT Alternaria solani |
| --- | --- | --- | --- | --- | --- |
| 1 | 500 | 100 | 45 | 100 | 100 |
|  | 100 | 100 | NT | NT | 70 |
|  | 20 | 100 | NT | NT | 32 |
| 2 | 500 | 100 | 25 | 60 | 79 |
|  | 100 | 0 | NT | NT | 25 |
|  | 20 | 0 | NT | NT | 25 |
| 5 | 500 | 100 | 0 | 85 | 70 |
| 6 | 500 | 0 | 0 | 0 | 0 |
| 7 | 500 | 0 | 0 | 0 | 35 |
| 8 | 500 | 100 | 50 | 100 | 40 |
| 9 | 500 | 50 | 45 | 35 | 20 |
| 10 | 500 | 100 | 0 | 90 | 80 |
| 11 | 500 | 100 | 0 | 100 | 90 |
| 12 | 500 | 100 | 0 | 85 | 100 |

| Compound No. | Dosage, ppm | POTATO/TOMATO LATE BLIGHT Phytophthora infestans | PEANUT WHITE MOLD Sclerotium rolfsii | GRAPE BUNCH ROT Botrytis cinerea | CEREAL LEAFSPOT Helminthosporium maydis |
| --- | --- | --- | --- | --- | --- |
| 1 | 500 | 100 | 75 | 100 | 100 |
|  | 100 | 76 | NT | 60 | 100 |
|  | 20 | 33 | NT | 43 | 100 |
| 2 | 500 | 80 | 55 | 72 | 100 |
|  | 100 | NT | NT | 16 | 100 |
|  | 20 | NT | NT | 0 | 42 |
| 5 | 500 | 100 | 0 | 60 | 100 |
| 6 | 500 | 20 | 0 | 25 | 40 |
| 7 | 500 | 0 | 0 | 50 | 25 |
| 8 | 500 | 100 | 50 | 100 | 90 |
| 9 | 500 | 90 | 45 | 20 | 65 |
| 10 | 500 | 95 | 0 | 100 | 85 |
| 11 | 500 | 100 | 0 | 100 | 100 |
| 12 | 500 | 100 | 55 | 100 | 95 |

EXAMPLE 12
Phytotoxicity Effect

All the plants subjected to treatment with the compounds of the present invention were evaluated to determine if their growth was adversely affected by such treatment. To determine this effect, the size and growth effects were noted for any of the plants treated with any of the compounds of this invention.

The above examples and embodiments will make apparent, to those skilled in the art, other embodiments and examples within the scope and spirit of this invention. These other embodiments and examples are within the contemplation of the instant invention. Therefore, the invention should be limited only by the appended claims.

What is claimed is:

1. A compound having the structural formula

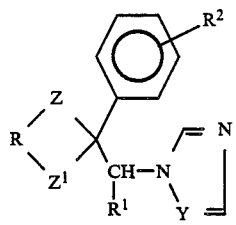

where Z is oxygen and $Z^1$ is sulfur, SO, or $SO_2$; Y is nitrogen or CH; R is linear or branched $C_2$-$C_{12}$ alkylene; $R^1$ is hydrogen, $C_1$-$C_4$ alkyl, benzyl or phenyl; $R^2$ is phenyl, phenoxy, phenylthio, phenylsulfinyl, phenylsulfonyl, phenylamino, benzyl, phenoxy substituted with halo, $C_1$-$C_4$ alkyl, $C_1$-$C_4$ alkoxy, nitro, cyano, trihalomethyl or mono-, di- or trihalomethoxy or phenyl substituted with halo, $C_1$-$C_4$ alkyl, $C_1$-$C_4$ alkoxy, nitro, cyano, trihalomethyl or mono-, di- or trihalomethoxy.

2. A compound in accordance with claim 1 where Y is nitrogen; Z is oxygen; $Z^1$ is sulfur or $SO_2$; R is linear or branched $C_2$-$C_5$ alkylene; $R^1$ is hydrogen, methyl or phenyl; and $R^2$ is phenyl, phenylthio, phenoxy, phenyl substituted with fluorine, chlorine, bromine, methyl, methoxy, trifluoromethyl or dichloromethoxy or phenoxy substituted with fluorine, chlorine, bromine, methyl, methoxy, trifluoromethyl or dichloromethoxy.

3. A compound in accordance with claim 2 wherein R is $C_2$ alkylene; $R^1$ is hydrogen; and $R^2$ is phenyl, phenylthio, phenoxy, phenyl substituted with bromine or phenoxy substituted with bromine.

4. A process for controlling fungi which comprises applying a fungicidally effective amount of the compound of claim 1.

5. A process for controlling fungi which comprises applying a fungicidally effective amount of the compound of claim 2.

6. A process for controlling fungi which comprises applying a fungicidally effective amount of the compound of claim 3.

7. A fungicidal composition comprising:
(a) a fungicidally effective amount of a compound having the structural formula:

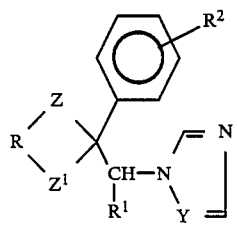

wherein:
Z is oxygen and $Z^1$ is sulfur, SO, or $SO_2$
Y is nitrogen or CH;
R is a linear or branched $C_2$-$C_{12}$ alkylene;
$R^1$ is hydrogen, $C_1$-$C_4$ alkyl, benzyl or phenyl;
$R^2$ is phenyl; phenoxy; phenylthio; phenylsulfinyl; phenylsulfonyl; phenylamino; benzyl; phenoxy substituted with halo, $C_1$-$C_4$ alkyl, $C_1$-$C_4$ alkoxy, nitro, cyano, trihalomethyl or mono-, di- or trihalomethoxy; or phenyl substituted with halo, $C_1$-$C_4$ alkyl, $C_1$-$C_4$ alkoxy, nitro, cyano, trihalomethyl or mono-, di or trihalomethoxy; and (b) at least one member of the group consisting of solid inert carriers and liquid inert carriers.

8. A fungicidal composition in accordance with claim 7 wherein, in component (a)
Y is nitrogen;
Z is oxygen;
$Z_1$ is sulfur or $SO_2$;
R is linear or branched $C_2$-$C_5$ alkylene;
$R^1$ is hydrogen, methyl or phenyl; and
$R^2$ is phenyl; phenylthio; phenoxy; phenyl substituted with fluorine, chlorine, bromine, methyl, methoxy, trifluoromethyl or dichloromethoxy; or phenoxy substituted with fluorine, chlorine, bromine, methyl, methoxy, trifluoromethyl or dichloromethoxy.

9. A fungicidal composition in accordance with claim 8 wherein, in component (a)
R is $C_2$ alkylene;
$R^1$ is hydrogen; and
$R^2$ is phenyl, phenylthio, phenoxy, phenyl substituted with bromine or phenoxy substituted with bromine.

* * * * *